United States Patent
Adawi et al.

(10) Patent No.: US 12,369,974 B2
(45) Date of Patent: Jul. 29, 2025

(54) TOUCH INDICATION OF BALLOON-CATHETER ABLATION ELECTRODE VIA BALLOON SURFACE TEMPERATURE MEASUREMENT

(71) Applicant: Biosense Webster (Israel) Ltd., Yokneam (IL)

(72) Inventors: Eid Adawi, Tur'an (IL); Iyar Rom, Givat haim ichud (IL); Nakdimon Nissim Levy, Pardes Hana (IL); Eliyahu Ravuna, Kiryat Ata (IL); Shmuel Auerbach, Kerem Maharal (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 1034 days.

(21) Appl. No.: 16/598,503

(22) Filed: Oct. 10, 2019

(65) Prior Publication Data

US 2021/0106382 A1 Apr. 15, 2021

(51) Int. Cl.
*A61B 18/14* (2006.01)
*A61B 5/00* (2006.01)
(Continued)

(52) U.S. Cl.
CPC ...... *A61B 18/1492* (2013.01); *A61B 5/14539* (2013.01); *A61B 5/6853* (2013.01);
(Continued)

(58) Field of Classification Search
CPC .......... A61B 18/1492; A61B 2090/065; A61B 5/14539; A61B 5/6853;
(Continued)

(56) References Cited

U.S. PATENT DOCUMENTS

| D123,782 S | 12/1940 | Paul |
| 3,316,896 A | 5/1967 | Louis |

(Continued)

FOREIGN PATENT DOCUMENTS

| CN | 101422637 A | 5/2009 |
| CN | 102271607 A | 12/2011 |

(Continued)

OTHER PUBLICATIONS

Extended European Search Report dated Mar. 22, 2021, from corresponding European Application No. 20201012.0.

(Continued)

*Primary Examiner* — Michael F Peffley
*Assistant Examiner* — Bo Ouyang

(57) ABSTRACT

A method includes positioning an expandable balloon, coupled to a distal end of a catheter, at a target location within an organ of a patient, the expandable balloon including multiple electrodes and one or more sensors in proximity to each electrode, wherein the one or more sensors are configured each to measure a characteristic of blood. The expandable balloon is expanded at the target location. A fluid is flowed through an inner lumen of the catheter and into the blood in a vicinity of each electrode. A dependence of the characteristic of blood on time is measured, via the one or more sensors, in proximity to each electrode. Using a processor, it is determined whether or not each electrode is in physical contact with tissue, based on the measured dependence of the characteristic of blood. An indication of whether or not each electrode is in physical contact with tissue is outputted to a user.

33 Claims, 3 Drawing Sheets

(51) Int. Cl.
*A61B 5/145* (2006.01)
*A61B 17/00* (2006.01)
*A61B 18/00* (2006.01)
*A61B 90/00* (2016.01)
*A61M 5/00* (2006.01)
*A61M 25/10* (2013.01)

(52) U.S. Cl.
CPC .............. *A61B 2017/00725* (2013.01); *A61B 2018/00029* (2013.01); *A61B 2018/00375* (2013.01); *A61B 2018/00577* (2013.01); *A61B 2018/00791* (2013.01); *A61B 2018/00875* (2013.01); *A61B 2090/065* (2016.02); *A61B 2218/002* (2013.01); *A61M 5/007* (2013.01); *A61M 2025/105* (2013.01)

(58) Field of Classification Search
CPC ........... A61B 2017/00725; A61B 2018/00029; A61B 2018/00375; A61B 2018/00577; A61B 2018/00791; A61B 2018/00875; A61B 2218/002; A61M 5/007; A61M 2025/105
See application file for complete search history.

(56) References Cited

U.S. PATENT DOCUMENTS

| | | |
|---|---|---|
| 4,276,874 A | 7/1981 | Wolvek et al. |
| 4,587,975 A | 5/1986 | Salo et al. |
| 4,709,698 A | 12/1987 | Johnston et al. |
| 4,805,621 A | 2/1989 | Heinze et al. |
| 5,178,957 A | 1/1993 | Kolpe et al. |
| 5,391,199 A | 2/1995 | Ben-Haim |
| 5,429,617 A | 7/1995 | Hammersmark et al. |
| 5,582,609 A | 12/1996 | Swanson et al. |
| 5,584,830 A | 12/1996 | Ladd et al. |
| 5,702,386 A | 12/1997 | Stern et al. |
| 5,718,241 A | 2/1998 | Ben-Haim et al. |
| 5,797,903 A | 8/1998 | Swanson et al. |
| 5,860,974 A | 1/1999 | Abele |
| 5,971,983 A | 10/1999 | Lesh |
| 6,012,457 A | 1/2000 | Lesh |
| 6,024,740 A | 2/2000 | Lesh et al. |
| 6,042,580 A | 3/2000 | Simpson |
| 6,123,718 A | 9/2000 | Tu et al. |
| 6,164,283 A | 12/2000 | Lesh |
| 6,171,275 B1 | 1/2001 | Webster, Jr. |
| 6,176,832 B1 | 1/2001 | Habu et al. |
| 6,198,974 B1 | 3/2001 | Webster, Jr. |
| 6,226,542 B1 | 5/2001 | Reisfeld |
| 6,239,724 B1 | 5/2001 | Doron et al. |
| 6,301,496 B1 | 10/2001 | Reisfeld |
| 6,322,558 B1 | 11/2001 | Taylor et al. |
| 6,332,089 B1 | 12/2001 | Acker et al. |
| 6,380,957 B1 | 4/2002 | Banning |
| 6,402,740 B1 | 6/2002 | Ellis et al. |
| D462,389 S | 9/2002 | Provence et al. |
| 6,471,693 B1 | 10/2002 | Carroll et al. |
| 6,484,118 B1 | 11/2002 | Govari |
| 6,522,930 B1 | 2/2003 | Schaer et al. |
| 6,618,612 B1 | 9/2003 | Acker et al. |
| 6,656,174 B1 | 12/2003 | Hegde et al. |
| 6,690,963 B2 | 2/2004 | Ben-Haim et al. |
| 6,814,733 B2 | 11/2004 | Schwartz et al. |
| 6,893,433 B2 | 5/2005 | Lentz |
| 6,986,744 B1 | 1/2006 | Krivitski |
| 6,987,995 B2 | 1/2006 | Drysen |
| 6,997,924 B2 | 2/2006 | Schwartz et al. |
| 7,142,903 B2 | 11/2006 | Rodriguez et al. |
| 7,156,816 B2 | 1/2007 | Schwartz et al. |
| 7,274,957 B2 | 9/2007 | Drysen |
| 7,340,307 B2 | 3/2008 | Maguire et al. |
| 7,377,906 B2 | 5/2008 | Selkee |
| 7,442,190 B2 | 10/2008 | Abboud et al. |
| 7,536,218 B2 | 5/2009 | Govari et al. |
| 7,591,799 B2 | 9/2009 | Selkee |
| 7,593,760 B2 | 9/2009 | Rodriguez et al. |
| 7,720,517 B2 | 5/2010 | Drysen |
| 7,756,576 B2 | 7/2010 | Levin |
| 7,842,031 B2 | 11/2010 | Abboud et al. |
| 7,853,302 B2 | 12/2010 | Rodriguez et al. |
| 8,000,765 B2 | 8/2011 | Rodriguez et al. |
| 8,021,327 B2 | 9/2011 | Selkee |
| 8,048,032 B2 | 11/2011 | Root et al. |
| 8,231,617 B2 | 7/2012 | Satake |
| 8,267,932 B2 | 9/2012 | Baxter et al. |
| 8,275,440 B2 | 9/2012 | Rodriguez et al. |
| 8,348,888 B2 | 1/2013 | Selkee |
| 8,357,152 B2 | 1/2013 | Govari et al. |
| D682,289 S | 5/2013 | DiJulio et al. |
| D682,291 S | 5/2013 | Baek et al. |
| D690,318 S | 9/2013 | Kluttz et al. |
| D694,652 S | 12/2013 | Tompkin |
| 8,641,709 B2 | 2/2014 | Sauvageau et al. |
| 8,721,590 B2 | 5/2014 | Seward et al. |
| 8,777,161 B2 | 7/2014 | Pollock et al. |
| D716,340 S | 10/2014 | Bresin et al. |
| 8,852,181 B2 | 10/2014 | Malecki et al. |
| D720,766 S | 1/2015 | Mandal et al. |
| D721,379 S | 1/2015 | Moon et al. |
| D724,618 S | 3/2015 | Shin |
| 8,998,893 B2 | 4/2015 | Avitall |
| D729,263 S | 5/2015 | Ahn et al. |
| 9,089,350 B2 | 7/2015 | Willard |
| D736,780 S | 8/2015 | Wang |
| 9,126,023 B1 | 9/2015 | Sahatjian et al. |
| D740,308 S | 10/2015 | Kim et al. |
| D743,424 S | 11/2015 | Danielyan et al. |
| D744,000 S | 11/2015 | Villamor et al. |
| 9,173,758 B2 | 11/2015 | Brister et al. |
| D747,742 S | 1/2016 | Fan et al. |
| D750,644 S | 3/2016 | Bhutani et al. |
| 9,283,034 B2 | 3/2016 | Katoh et al. |
| 9,289,141 B2 | 3/2016 | Lowery et al. |
| D753,690 S | 4/2016 | Vazquez et al. |
| 9,320,631 B2 | 4/2016 | Moore et al. |
| 9,345,540 B2 | 5/2016 | Mallin et al. |
| D759,673 S | 6/2016 | Looney et al. |
| D759,675 S | 6/2016 | Looney et al. |
| D764,500 S | 8/2016 | Wang |
| D765,709 S | 9/2016 | Gagnier |
| D767,616 S | 9/2016 | Jones et al. |
| D768,696 S | 10/2016 | Gagnier |
| D783,037 S | 4/2017 | Hariharan et al. |
| 9,655,677 B2 | 5/2017 | Salahieh et al. |
| D791,805 S | 7/2017 | Segars |
| 9,795,442 B2 | 10/2017 | Salahieh et al. |
| 9,907,610 B2 | 3/2018 | Beeckler et al. |
| 9,956,035 B2 | 5/2018 | Govari et al. |
| D861,717 S | 10/2019 | Brekke et al. |
| 10,688,278 B2 | 6/2020 | Beeckler et al. |
| 2001/0031961 A1 | 10/2001 | Hooven |
| 2002/0002369 A1 | 1/2002 | Hood |
| 2002/0065455 A1 | 5/2002 | Ben-Haim et al. |
| 2002/0068931 A1 | 6/2002 | Wong et al. |
| 2002/0077627 A1 | 6/2002 | Johnson et al. |
| 2002/0160134 A1 | 10/2002 | Ogushi et al. |
| 2003/0018327 A1 | 1/2003 | Truckai et al. |
| 2003/0028183 A1 | 2/2003 | Sanchez et al. |
| 2003/0050637 A1 | 3/2003 | MaGuire et al. |
| 2003/0060820 A1 | 3/2003 | MaGuire et al. |
| 2003/0120150 A1 | 6/2003 | Govari |
| 2003/0144658 A1 | 7/2003 | Schwartz et al. |
| 2004/0068178 A1 | 4/2004 | Govari |
| 2004/0122445 A1 | 6/2004 | Butler et al. |
| 2004/0147920 A1 | 7/2004 | Keidar |
| 2004/0225285 A1 | 11/2004 | Gibson |
| 2005/0070887 A1 | 3/2005 | Taimisto et al. |
| 2005/0119686 A1 | 6/2005 | Clubb |
| 2006/0013595 A1 | 1/2006 | Trezza et al. |
| 2006/0106375 A1 | 5/2006 | Werneth et al. |
| 2006/0135953 A1 | 6/2006 | Kania et al. |
| 2007/0071792 A1 | 3/2007 | Varner et al. |
| 2007/0080322 A1 | 4/2007 | Walba |

(56) References Cited

U.S. PATENT DOCUMENTS

| | | |
|---|---|---|
| 2007/0083194 A1 | 4/2007 | Kunis et al. |
| 2007/0287994 A1 | 12/2007 | Patel |
| 2008/0018891 A1 | 1/2008 | Hell et al. |
| 2008/0021313 A1 | 1/2008 | Eidenschink et al. |
| 2008/0051707 A1 | 2/2008 | Phan et al. |
| 2008/0097422 A1 | 4/2008 | Edwards et al. |
| 2008/0140072 A1 | 6/2008 | Stangenes et al. |
| 2008/0183132 A1 | 7/2008 | Davies et al. |
| 2008/0188912 A1 | 8/2008 | Stone et al. |
| 2008/0202637 A1 | 8/2008 | Hector et al. |
| 2008/0208186 A1 | 8/2008 | Slater |
| 2008/0249463 A1 | 10/2008 | Pappone et al. |
| 2008/0262489 A1 | 10/2008 | Steinke |
| 2008/0281312 A1 | 11/2008 | Werneth et al. |
| 2009/0163890 A1 | 6/2009 | Clifford et al. |
| 2009/0182318 A1 | 7/2009 | Abboud et al. |
| 2009/0270850 A1 | 10/2009 | Zhou et al. |
| 2009/0312617 A1* | 12/2009 | Creed ............... A61B 17/3478 600/509 |
| 2010/0069836 A1 | 3/2010 | Satake |
| 2010/0114269 A1 | 5/2010 | Wittenberger et al. |
| 2010/0204560 A1 | 8/2010 | Salahieh et al. |
| 2010/0256629 A1 | 10/2010 | Wylie et al. |
| 2010/0324552 A1 | 12/2010 | Kauphusman et al. |
| 2011/0118632 A1 | 5/2011 | Sinelnikov et al. |
| 2011/0130648 A1 | 6/2011 | Beeckler et al. |
| 2011/0144637 A1* | 6/2011 | Pageard ............... A61B 5/6869 606/41 |
| 2011/0282338 A1 | 11/2011 | Fojtik |
| 2011/0295248 A1 | 12/2011 | Wallace et al. |
| 2011/0301587 A1 | 12/2011 | Deem et al. |
| 2011/0313286 A1 | 12/2011 | Whayne et al. |
| 2012/0019107 A1 | 1/2012 | Gabl et al. |
| 2012/0029511 A1 | 2/2012 | Smith et al. |
| 2012/0065503 A1 | 3/2012 | Rogers et al. |
| 2012/0071870 A1 | 3/2012 | Salahieh et al. |
| 2012/0079427 A1 | 3/2012 | Carmichael et al. |
| 2012/0101413 A1* | 4/2012 | Beetel ............... A61B 18/1492 601/3 |
| 2012/0101538 A1 | 4/2012 | Ballakur et al. |
| 2012/0143177 A1 | 6/2012 | Avitall |
| 2012/0143293 A1 | 6/2012 | Mauch et al. |
| 2012/0191079 A1 | 7/2012 | Moll et al. |
| 2012/0209260 A1 | 8/2012 | Lambert et al. |
| 2013/0085360 A1 | 4/2013 | Grunewald |
| 2013/0090649 A1 | 4/2013 | Smith et al. |
| 2013/0109982 A1 | 5/2013 | Sato et al. |
| 2013/0150693 A1 | 6/2013 | D'Angelo et al. |
| 2013/0165916 A1 | 6/2013 | Mathur et al. |
| 2013/0165941 A1 | 6/2013 | Murphy |
| 2013/0165990 A1 | 6/2013 | Mathur et al. |
| 2013/0169624 A1 | 7/2013 | Bourier et al. |
| 2013/0261692 A1 | 10/2013 | Cardinal et al. |
| 2013/0274562 A1 | 10/2013 | Ghaffari et al. |
| 2013/0274658 A1 | 10/2013 | Steinke et al. |
| 2013/0282084 A1 | 10/2013 | Mathur et al. |
| 2013/0318439 A1 | 11/2013 | Landis et al. |
| 2014/0012242 A1 | 1/2014 | Lee et al. |
| 2014/0018788 A1 | 1/2014 | Engelman et al. |
| 2014/0031813 A1 | 1/2014 | Tellio et al. |
| 2014/0058197 A1 | 2/2014 | Salahieh et al. |
| 2014/0121470 A1 | 5/2014 | Scharf et al. |
| 2014/0148805 A1 | 5/2014 | Stewart et al. |
| 2014/0180077 A1* | 6/2014 | Huennekens ............... A61B 8/12 600/407 |
| 2014/0227437 A1 | 8/2014 | DeBoer et al. |
| 2014/0243821 A1 | 8/2014 | Salahieh et al. |
| 2014/0275993 A1 | 9/2014 | Ballakur |
| 2014/0276709 A1* | 9/2014 | Wittenberger ......... A61B 18/02 606/34 |
| 2014/0276756 A1 | 9/2014 | Hill |
| 2014/0276789 A1 | 9/2014 | Dandler et al. |
| 2014/0276811 A1 | 9/2014 | Koblish et al. |
| 2014/0288546 A1 | 9/2014 | Sherman et al. |
| 2014/0330266 A1 | 11/2014 | Thompson et al. |
| 2014/0357956 A1 | 12/2014 | Salahieh et al. |
| 2015/0005799 A1 | 1/2015 | Lindquist et al. |
| 2015/0025532 A1 | 1/2015 | Hanson et al. |
| 2015/0025533 A1 | 1/2015 | Groff et al. |
| 2015/0057655 A1 | 2/2015 | Osypka |
| 2015/0067512 A1 | 3/2015 | Roswell |
| 2015/0080883 A1 | 3/2015 | Haverkost et al. |
| 2015/0105774 A1 | 4/2015 | Lindquist et al. |
| 2015/0112256 A1 | 4/2015 | Byrne et al. |
| 2015/0112321 A1* | 4/2015 | Cadouri ............ A61B 18/1492 606/34 |
| 2015/0119875 A1 | 4/2015 | Fischell et al. |
| 2015/0141982 A1 | 5/2015 | Lee |
| 2015/0157382 A1 | 6/2015 | Avitall et al. |
| 2015/0216591 A1 | 8/2015 | Cao et al. |
| 2015/0216650 A1 | 8/2015 | Shaltis |
| 2015/0223704 A1* | 8/2015 | Haverkost ............ A61B 5/6856 623/1.11 |
| 2015/0265329 A1 | 9/2015 | Lalonde et al. |
| 2015/0265339 A1 | 9/2015 | Lindquist et al. |
| 2015/0265812 A1 | 9/2015 | Lalonde |
| 2015/0272667 A1 | 10/2015 | Govari et al. |
| 2015/0327805 A1 | 11/2015 | Ben-Haim |
| 2015/0341752 A1 | 11/2015 | Flynn |
| 2016/0000499 A1 | 1/2016 | Lennox et al. |
| 2016/0051321 A1 | 2/2016 | Salahieh et al. |
| 2016/0085431 A1 | 3/2016 | Kim et al. |
| 2016/0106499 A1 | 4/2016 | Ogata et al. |
| 2016/0157914 A1 | 6/2016 | Avitall |
| 2016/0166306 A1 | 6/2016 | Pageard |
| 2016/0175041 A1 | 6/2016 | Govari et al. |
| 2016/0196635 A1 | 7/2016 | Cho et al. |
| 2016/0256076 A1* | 9/2016 | Kassab ............ A61B 5/6853 |
| 2016/0256305 A1 | 9/2016 | Longo et al. |
| 2016/0374748 A9 | 12/2016 | Salahieh et al. |
| 2017/0042614 A1 | 2/2017 | Salahieh et al. |
| 2017/0042615 A1 | 2/2017 | Salahieh et al. |
| 2017/0080192 A1 | 3/2017 | Giasolli et al. |
| 2017/0143359 A1 | 5/2017 | Nguyen et al. |
| 2017/0164464 A1 | 6/2017 | Weinkam et al. |
| 2017/0311829 A1 | 11/2017 | Beeckler et al. |
| 2017/0311893 A1 | 11/2017 | Beeckler et al. |
| 2017/0312022 A1 | 11/2017 | Beeckler et al. |
| 2017/0347896 A1 | 12/2017 | Keyes et al. |
| 2018/0074693 A1 | 3/2018 | Jones et al. |
| 2018/0110562 A1 | 4/2018 | Govari et al. |
| 2018/0125575 A1 | 5/2018 | Schwartz et al. |
| 2018/0256247 A1 | 9/2018 | Govari et al. |
| 2018/0280080 A1 | 10/2018 | Govari et al. |
| 2018/0310978 A1 | 11/2018 | Avitall |
| 2018/0333162 A1 | 11/2018 | Saab |
| 2018/0368927 A1 | 12/2018 | Lyons et al. |
| 2019/0059818 A1 | 2/2019 | Herrera et al. |
| 2019/0060622 A1 | 2/2019 | Beeckler |
| 2019/0143079 A1 | 5/2019 | Beeckler et al. |
| 2019/0175262 A1 | 6/2019 | Govari et al. |
| 2019/0175263 A1 | 6/2019 | Altmann et al. |
| 2019/0183567 A1 | 6/2019 | Govari et al. |
| 2019/0201669 A1 | 7/2019 | Govari et al. |
| 2019/0217065 A1 | 7/2019 | Govari et al. |
| 2019/0297441 A1 | 9/2019 | Dehe et al. |
| 2019/0298441 A1 | 10/2019 | Clark et al. |
| 2019/0365451 A1 | 12/2019 | Jung, Jr. |
| 2020/0001054 A1 | 1/2020 | Jimenez et al. |
| 2020/0015693 A1 | 1/2020 | Beeckler et al. |
| 2020/0085497 A1 | 3/2020 | Zhang et al. |
| 2020/0155226 A1 | 5/2020 | Valls et al. |
| 2021/0169567 A1 | 6/2021 | Govari et al. |

FOREIGN PATENT DOCUMENTS

| | | |
|---|---|---|
| CN | 102458566 A | 5/2012 |
| CN | 203539434 U | 4/2014 |
| CN | 104244856 A | 12/2014 |
| CN | 104546117 A | 4/2015 |
| CN | 105105844 A | 12/2015 |
| CN | 105473091 A | 4/2016 |
| CN | 105473093 A | 4/2016 |

(56) References Cited

FOREIGN PATENT DOCUMENTS

| | | |
|---|---|---|
| CN | 108175400 A | 6/2018 |
| EP | 0779059 A1 | 6/1997 |
| EP | 1790304 A2 | 5/2007 |
| EP | 2749214 A1 | 7/2014 |
| EP | 2865350 A2 | 4/2015 |
| EP | 2875790 A2 | 5/2015 |
| EP | 2370015 B1 | 12/2016 |
| EP | 3238646 A2 | 11/2017 |
| EP | 3238648 A1 | 11/2017 |
| EP | 3251622 A1 | 12/2017 |
| EP | 3300680 A1 | 4/2018 |
| EP | 3315087 A1 | 5/2018 |
| EP | 3332727 A2 | 6/2018 |
| EP | 3571983 A2 | 11/2019 |
| EP | 3586778 A1 | 1/2020 |
| EP | 3653153 A1 | 5/2020 |
| EP | 3682799 A2 | 7/2020 |
| JP | H06261951 A | 9/1994 |
| JP | H1176233 A | 3/1999 |
| JP | 2000504242 A | 4/2000 |
| JP | 2005052424 A | 3/2005 |
| JP | 2009500052 A | 1/2009 |
| JP | 2010507404 A | 3/2010 |
| JP | 2012024156 A | 2/2012 |
| JP | 2013013726 A | 1/2013 |
| JP | 2013078587 A | 5/2013 |
| JP | 2013529109 A | 7/2013 |
| JP | 2014529419 A | 11/2014 |
| JP | 2015503365 A | 2/2015 |
| JP | 2015100706 A | 6/2015 |
| JP | 2015112113 A | 6/2015 |
| JP | 2015112114 A | 6/2015 |
| JP | 2015518776 A | 7/2015 |
| JP | 2016515442 A | 5/2016 |
| JP | 2016116863 A | 6/2016 |
| JP | 2017136356 A | 8/2017 |
| JP | 2017217473 A | 12/2017 |
| WO | WO 96/05768 | 2/1996 |
| WO | 0056237 A2 | 9/2000 |
| WO | 02102231 A2 | 12/2002 |
| WO | 2005041748 A2 | 5/2005 |
| WO | 2008049087 A2 | 4/2008 |
| WO | 2011143468 A2 | 11/2011 |
| WO | 2013049601 A2 | 4/2013 |
| WO | 2013052919 A2 | 4/2013 |
| WO | 2013154776 A2 | 10/2013 |
| WO | 2014168987 A1 | 10/2014 |
| WO | 2015049784 A1 | 4/2015 |
| WO | 2016086313 A1 | 6/2016 |
| WO | 2016183337 A2 | 11/2016 |
| WO | 2016210437 A1 | 12/2016 |
| WO | 2017024306 A1 | 2/2017 |
| WO | 2017087549 A1 | 5/2017 |
| WO | 2018106569 A1 | 6/2018 |
| WO | 2018129133 A1 | 7/2018 |
| WO | 2019023280 A1 | 1/2019 |
| WO | 2019095020 A1 | 5/2019 |

OTHER PUBLICATIONS

Angela O., "AF Symposium 2017: First-in-Man Study Shows Promising Results with a Multi-Electrode Radiofrequency Balloon for Paroxysmal AF Treatment," Cardiac Rhythm News, Jan. 20, 2017, 2 Pages, [Retrieved on Dec. 16, 2020] Retrieved from URL: https://cardiacrhythmnews.com/fist-in-man-study-shows-promising-results-with-a-multi-electrode-radiofrequency-balloon-for-paroxysmal-af-treatment/.

Casella M., et al., "Ablation Index as a Predictor of Long-Term Efficacy in Premature Ventricular Complex Ablation: A Regional Target Value Analysis," Heart Rhythm Society, Jun. 2019, vol. 16, No. 6, pp. 888-895.

Co-Pending U.S. Appl. No. 14/578,807, filed Dec. 22, 2014, 21 pages.

Das M., et al., "Ablation Index, a Novel Marker of Ablation Lesion Quality: Prediction of Pulmonary Vein Reconnection at Repeat Electrophysiology Study and Regional Differences in Target Values," Europace, 2017, Published Online May 31, 2016, vol. 19, pp. 775-783.

Dorobantu M., et al., "Oral Anticoagulation During Atrial Fibrillation Ablation: Facts and Controversies," Cor et Vasa, 2013, Accepted on Dec. 3, 2012, vol. 55, No. 2, pp. e101-e106, Retrieved from URL: https://www.sciencedirect.com/science/article/pii/S0010865012001415.

Extended European Search Report for Application No. EP17168513.4 mailed Sep. 18, 2017, 11 pages.

Extended European Search Report for European Application No. 15201723.2, mailed May 11, 2016, 07 Pages.

Extended European Search Report for European Application No. 17168393.1 mailed Dec. 15, 2017, 12 Pages.

Extended European Search Report for European Application No. 17168518.3, mailed Sep. 20, 2017, 9 Pages.

Extended European Search Report for European Application No. 17173893.3, mailed Nov. 6, 2017, 8 Pages.

Extended European Search Report for European Application No. 17201434.2, mailed Feb. 1, 2018, 10 Pages.

Extended European Search Report for European Application No. 17205876.0, mailed Jun. 1, 2018, 13 Pages.

Extended European Search Report for European Application No. 19177365.4, mailed Nov. 8, 2019, 07 Pages.

Extended European Search Report for European Application No. 19183327.6, mailed Nov. 21, 2019, 8 Pages.

Extended European Search Report for European Application No. 20153872.5, mailed May 7, 2020, 9 Pages.

Extended European Search Report for European Application No. 20195648.9, mailed Feb. 12, 2021, 8 Pages.

Fornell D., "Multi-Electrode RF Balloon Efficient for Acute Pulmonary Vein Isolation," Diagnostic and Interventional Cardiology, May 17, 2017, 3 Pages, [Retrieved on Dec. 16, 2020] Retrieved from URL: www.dicardiology.com/article/multi-electrode-rf-balloon-efficient-acute-pulmonary-vein-isolation.

Haines D.E., et al., "The Promise of Pulsed Field Ablation," Dec. 2019, vol. 19, No. 12, 10 pages.

Honarbakhsh S., et al., "Radiofrequency Balloon Catheter Ablation for Paroxysmal Atrial Fibrillation, Radiance Study—a UK experience," EP Europace, Oct. 2017, vol. 19, No. 1, p. i21, 3 Pages.

International Search Report and Written Opinion for International Application No. PCT/IB2019/052313, mailed Jul. 22, 2019, 8 Pages.

International Search Report and Written Opinion for International Application No. PCT/IB2019/056381, mailed Dec. 17, 2019, 10 pages.

International Search Report and Written Opinion for International Application No. PCT/IB2019/057743, mailed Dec. 6, 2019, 16 Pages.

International Search Report and Written Opinion issued in corresponding International Application No. PCT/IB2019/057742, dated Nov. 28, 2019, 18 Pages.

Nagashima K., et al., "Hot Balloon Versus Cryoballoon Ablation for Atrial Fibrillation," Circulation: Arrhythmia and Electrophysiology, May 2018, vol. 11, No. 5, e005861, 9 Pages.

Napoli N., et al., "For Atrial Fibrillation Ablation, Newer Anticoagulant Reduces Major Bleeds," American College of Cardiology, Mar. 19, 2017, 4 Pages, [Retrieved on Jan. 21, 2022] Retrieved from URL: https://www.acc.org/about-acc/press-releases/2017/03/18/08/47/sun-1045am-for-atrial-fibrillation-ablation-newer-anticoagulant-reduces-major-bleeds.

Okano T., et al., "Wire Perforation Causing Cardiopulmonary Arrest During Radiofrequency Hot Balloon Ablation for Pulmonary Vein Isolation," Journal of Cardiology Cases, Feb. 15, 2019, vol. 19, No. 5, pp. 169-172.

Partial European Search Report for European Application No. 17168393.1 mailed Sep. 13, 2017, 13 Pages.

Partial European Search Report for European Application No. 17205876.0, mailed Feb. 22, 2018, 10 Pages.

(56) References Cited

OTHER PUBLICATIONS

Reddy V.Y., et al., "Balloon Catheter Ablation to Treat Paroxysmal Atrial Fibrillation: What is the Level of Pulmonary Venous Isolation?," Heart Rhythm, Mar. 2008, vol. 5, No. 3, pp. 353-360, 3 Pages.
Winkle R.A., et al., "Atrial Fibrillation Ablation Using Open-Irrigated Tip Radiofrequency: Experience with Intraprocedural Activated Clotting Times ≤ 210 Seconds," Heart Rhythm, Jun. 2014, Epub Mar. 27, 2014, vol. 11, No. 6, pp. 963-968.
Youtube:, "Intensity™ CX4 Professional E-Stim/ Ultrasound Combo," Dec. 22, 2015, 1 Page, [Retrieved on Nov. 19, 2020], Retrieved from URL: https://www.youtube.com/watch?v=76s1QKMWJME].
Youtube: "New Interface TactiCath Contact Force Ablation Catheter," Nov. 26, 2013, 1 Pages, [Retrieved on Nov. 19, 2020], Retrieved from URL: https: /Avww.youtube.com/watch?v=aYvYO8Hpylg].
English translation of Search Report dated Mar. 27, 2024, from corresponding Japanese Application No. 2020-171000.
English translation of Notice of Reasons for Refusal dated Apr. 2, 2024, from corresponding Japanese Application No. 2020-171000.
English translation of Decision to Grant a Patent dated Jul. 2, 2024, from corresponding Japanese Application No. 2020-171000.
First Office Action with English translation dated Apr. 15, 2025, from corresponding Chinese Application No. 202011072381.6.
First Search dated Apr. 15, 2025, from corresponding Chinese Application No. 202011072381.6.

\* cited by examiner

TOUCH INDICATION OF BALLOON-CATHETER ABLATION ELECTRODE VIA BALLOON SURFACE TEMPERATURE MEASUREMENT

FIELD OF THE INVENTION

The present invention relates generally to medical probes, and particularly to cardiac radiofrequency (RF) balloon ablation catheters.

BACKGROUND OF THE INVENTION

Medical probes equipped with biophysical sensors at their distal end were previously proposed in the patent literature. For example, U.S. Patent Application Publication 2014/0276709 describes a medical system, comprising an ablation catheter. The ablation catheter includes an elongate shaft with a proximal end, a distal end and a lumen disposed between the proximal end and the distal end. The ablation catheter also includes an inflatable element in fluid communication with the lumen, a first temperature sensor operable to measure a first temperature; and a second temperature sensor operable to measure a second temperature. The first temperature sensor and the second temperature sensor are longitudinally separated from each other by at least a portion of the inflatable element. Using a continuous flow of inflation fluid, the temperature differential between the first temperature measured at the first temperature sensor and the second temperature measured at the second temperature sensor is maintained. Maintaining the temperature differential may make occlusion assessment easier. Specifically, when there is complete occlusion, the first temperature at first temperature sensor will be a couple of degrees Celsius lower than the second temperature at second temperature sensor.

As another example, U.S. Patent Application Publication 2016/0157914 describes a method, system, and device for predicting lesion quality. Specifically, lesion quality may be predicted based on an assessment of pulmonary vein occlusion using saline injection and evaluation of temperature measurements recorded by a thermocouple located distal to a cryo-balloon of the treatment device. The quality of the occlusion may be rated based on the time it takes the temperature recorded by the thermocouple to increase from approximately 32° C. to approximately 38° C., the rate of temperature change over a predetermined time period, and/or the rate of dissipation within the pulmonary vein of the saline with a volume of contrast medium. For example, the quality of the occlusion may be rated as being good, fair, or poor. This assessment may be quickly and easily communicated to an operator.

U.S. Patent Application Publication 2008/0097422 describes systems and methods that deploy an electrode structure in contact with the tissue region. The electrode structure carries a sensor at a known location on the electrode structure to monitor an operating condition. The systems and methods provide an interface, which generate an idealized image of the electrode structure and an indicator image to represent the monitored operating condition in a spatial position on the idealized image corresponding to the location of the sensor on the electrode structure. The interface displays a view image comprising the idealized image and indicator image. The systems and methods cause the electrode structure to apply energy to heat the tissue region while the view image is displayed on the display screen. In an embodiment, each electrode carries one or more temperature sensors. Each electrode can carry two temperature sensors, one to sense temperature conditions near the exposed distal end of the electrode, and the other to sense temperature conditions in an electrically insulated location outside the electrode.

SUMMARY OF THE INVENTION

An embodiment of the present invention provides a method including positioning an expandable balloon, coupled to a distal end of a catheter, at a target location within an organ of a patient, the expandable balloon including multiple electrodes and one or more sensors in proximity to each electrode, wherein the one or more sensors are configured each to measure a characteristic of blood. The expandable balloon is expanded at the target location. A fluid is flowed through an inner lumen of the catheter and into the blood in a vicinity of each electrode. A dependence of the characteristic of blood on time is measured, via the one or more sensors, in proximity to each electrode. Using a processor, it is determined whether or not each electrode is in physical contact with tissue, based on the measured dependence of the characteristic of blood. An indication of whether or not each electrode is in physical contact with tissue is outputted to a user.

In some embodiments, flowing the fluid includes continuously applying irrigation fluid via the balloon. In other embodiments, flowing the fluid includes bolus-injecting the fluid.

In some embodiments, each of the one or more sensors includes a temperature sensor, and the characteristic of blood includes temperature.

In an embodiment, each of the one or more sensors includes a first electrode and a second electrode, and the characteristic of blood includes bipolar electrical impedance. In another embodiment, each of the one or more sensors includes a first electrode and a second electrode, the second electrode being a reference electrode, and the characteristic of blood includes unipolar electrical impedance.

In some embodiments, each of the one or more sensors includes a pH sensor, and the characteristic of blood includes pH.

In some embodiments, determining whether or not each electrode is in physical contact with tissue includes determining a baseline of the characteristic of blood, and comparing the baseline to the measured dependence on time.

In an embodiment, determining the baseline includes measuring the characteristic of blood using the one or more sensors of an electrode deliberately maneuvered not to be in contact with tissue.

In some embodiments, determining whether or not each electrode is in physical contact with tissue includes estimating a rate with which the characteristic of blood returns to an original value after stopping flow of the fluid. In other embodiments, determining whether or not each electrode is in physical contact with tissue includes estimating a time duration from a beginning of flow of the fluid until the characteristic of blood reaches a steady-state value.

In an embodiment, determining whether or not each electrode is in physical contact with tissue includes determining an extremum value of the characteristic of blood reached in vicinity of each electrode.

In another embodiment, measuring the dependence of the characteristic includes comparing the characteristic with a calibrated characteristic.

In some embodiments, the fluid includes a coolant.
In some embodiments, the fluid includes saline.

In an embodiment, flowing the fluid includes injecting the fluid through a lumen used for injecting contrast fluid. In another embodiment, flowing the fluid includes injecting the fluid through irrigation holes in the balloon.

In some embodiments, the cavity includes one of a pulmonary vein of the heart and a left atrium of the heart.

There is additionally provided, in accordance with an embodiment of the present invention, a system including a catheter and a processor. The catheter includes a shaft for insertion into a cavity of an organ of a patient at a target location within the organ, the shaft having an inner lumen for flowing a fluid to cause a transient characteristic of blood. The catheter further includes an expandable balloon, coupled to a distal end of the shaft, the expandable balloon including multiple electrodes and one or more sensors in proximity to each electrode, wherein the one or more sensors are configured each to measure the characteristic of blood. The processor is configured to determine whether or not each electrode is in physical contact with tissue, based on the measured dependence of the characteristic of blood, and output to a user an indication of whether or not each electrode is in physical contact with tissue.

The present invention will be more fully understood from the following detailed description of the embodiments thereof, taken together with the drawings in which:

DETAILED DESCRIPTION OF EMBODIMENTS

Overview

Figure 1:
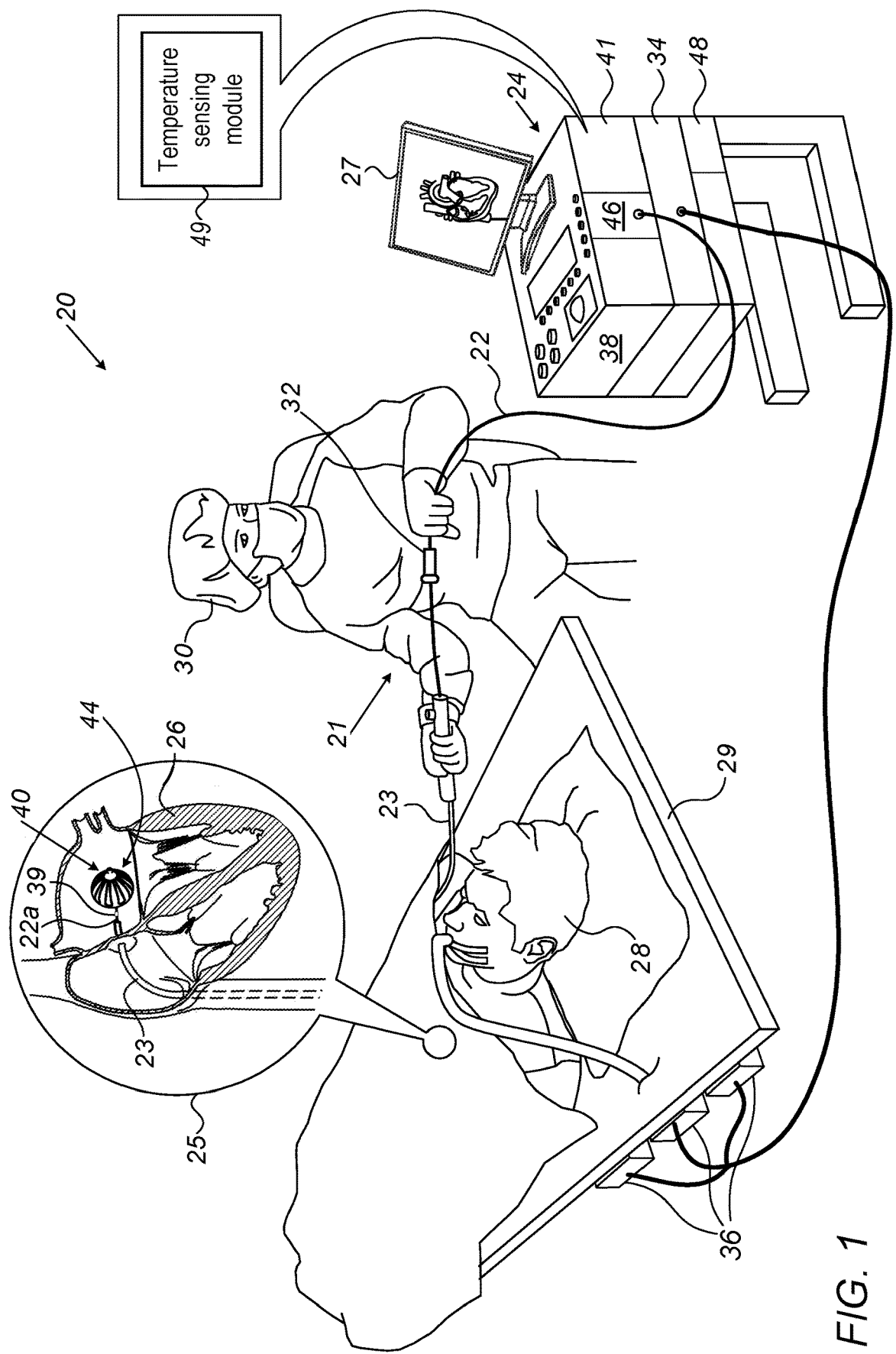
FIG. 1 is a schematic, pictorial illustration of a catheter-based position-tracking and balloon-ablation system, in accordance with an embodiment of the present invention.

For efficient ablation with a medical probe, such as an intra-cardiac balloon catheter, it is important that the ablating electrodes disposed over the balloon are in good physical contact with the tissue before tissue is being ablated. For example, for pulmonary vein (PV) isolation, all ablation electrodes should be in good contact over a perimeter of an ostium of the PV. However, checking for good contact with tissue, such as that of an ostium, for example by checking for occlusion of a distal blood vessel (e.g., of the PV), is tedious and conventionally relies on another modality, such as fluoroscopy. Furthermore, if there is not full occlusion, it is difficult, using fluoroscopy, to identify which specific ablation electrodes do not have good tissue contact.

Embodiments of the present invention that are described herein provide improved techniques for monitoring, e.g., immediately before ablation, whether and how well ablation electrodes of a cardiac balloon touch tissue. The disclosed techniques provide systems and methods that can estimate the degree of physical contact of an electrode using local irrigation and/or injection of fluid with different properties than blood, and measuring a resulting transient change in blood properties. Based on the sensed transient change in blood properties, a processor can determine whether or not each ablation electrode of a balloon ablation catheter is touching tissue.

In some embodiments, a system is provided, which includes a catheter including (i) a shaft for insertion into a cavity of an organ of a patient at a target location within the organ, the shaft having an inner lumen, wherein the inner lumen is configured to flow through a fluid to cause a transient characteristic of blood, and (ii) an expandable balloon, coupled to a distal end of the shaft, the expandable balloon comprising multiple electrodes and one or more sensors in proximity to each electrode, wherein the one or more sensors are configured each to measure the characteristic of blood. The system further includes a processor, which is configured to (a) determine whether or not each electrode is in physical contact with tissue, based on the measured dependence of the characteristic of blood and, (b) output to a user an indication of whether or not each electrode is in physical contact with tissue.

In an embodiment, the processor determines whether or not each electrode is in physical contact with tissue by determining a baseline of the characteristic of blood, and comparing the baseline to the measured dependence on time. In some cases, determining the baseline comprises measuring the characteristic of blood using the one or more sensors of an electrode deliberately maneuvered not to be in contact with tissue.

In some embodiments, the processor determines whether or not each electrode is in physical contact with tissue by estimating a rate with which the characteristic of blood returns to an original value after stopping injection of the fluid. In another embodiment, determining whether or not each electrode is in physical contact with tissue comprises determining an extremum value of the characteristic of blood reached in vicinity of each electrode.

In some embodiments, each of the one or more sensors comprises a temperature sensor and the characteristic of blood comprises temperature. A fluid that has a cooling effect on blood, such as saline solution, is pumped out of the balloon through irrigation holes into the blood stream. One or more temperature sensors disposed on each of the ablation electrodes of the balloon acquire the temperature vs. time (of each of the electrodes) after the release of fluid. The temperature profile (temperature variation over time) is different depending on whether or not the electrode is in good contact with tissue.

In another embodiment, to achieve an enhanced transient effect on temperature, a cooling fluid, e.g., saline or glucose solutions at low temperature, can be injected through a separate lumen, such as a lumen used to inject contrast fluid.

In an embodiment, measuring a dependence of the characteristic of blood on time in proximity to each electrode comprises comparing the characteristic with a calibrated characteristic. For example, A coolant is prepared having a given lower temperature compared with blood temperature in body. After coolant injection, a resulting peak difference between temperature of electrodes in contact with tissue and with blood can be calibrated with respect to the original coolant temperature. Based the calibration, the physician in the field has a predication on the expected peak difference in electrode temperature that indicates physical contact between electrode and tissue was indeed achieved.

Other physical effects may be generated, sensed, and analyzed using the disclosed technique, mutatis mutandis. For example, the pumped or injected fluid may locally affect the blood pH, and pH sensors disposed on each of the ablation electrodes of the balloon acquire the different pH vs. time (of each of the electrodes) after the release of fluid. As another example, the pumped or injected fluid may locally affect the $CO_2$ content of blood, and $CO_2$ sensors disposed on each of the ablation electrodes of the balloon acquire the different $PCO_2$ vs. time (of each of the electrodes) after the release of fluid. $PCO_2$ is defined herein as partial pressure of carbon dioxide in blood. The peak and/or steady state difference in each of the above physical effects is also related to the difference between these values (i) in blood, (ii) in body and (iii) in fluid outside the body, and these relations can be calibrated. A predication can be made on the expected peak difference, and the predication used to indicate a level of physical contact.

In an embodiment, a sensor made of two electrodes measures changes in bipolar electrical impedance as a function of a transient blood property that has different effects on inter-electrode impedance via blood and via cardiac tissue. In another embodiment, a sensor uses one electrode and a reference electrode to measure unipolar electrical impedance as a function of transient blood properties. For example, impedance of blood may change in the presence of pumped saline, and measuring both impedance and temperature profiles with two different sensors may further improve the technique.

In some embodiments, based on the disclosed technique, the processor is further configured to provide a touch value on a scale between no-touch and full-touch, and to visually indicate the touch value for every electrode of the balloon.

By providing tissue touch indication per electrode, over the entire perimeter of an ablation balloon, the disclosed technique can improve accuracy of the balloon catheter positioning against tissue and thereby improve effectiveness of balloon ablation. Furthermore, the disclosed technique does not require X-ray fluoroscopy imaging with use of contrast material, and is therefore safer for both patients and physicians.

The disclosed technique thus provides complete and safe real-time assessment of individual balloon electrode touch with tissue, which may improve the outcome of cardiac balloon ablation treatments, such as of pulmonary vein (PV) isolation, as a treatment of arrhythmia.

System Description

FIG. 1 is a schematic, pictorial illustration of a catheter-based position-tracking and balloon-ablation system 20, in accordance with an embodiment of the present invention. System 20 comprises a catheter 21 that, as seen in inset 25, is fitted at a distal end 22a of a shaft 22 of the catheter with an RF ablation expandable balloon 40. As further shown in inset 25, distal end 22a comprises a magnetic sensor 39, contained within distal end 22a just proximally to expandable balloon 40.

The proximal end of catheter 21 is connected to a control console 24. Console 24 includes an irrigation module 46 allowing system 20 to control irrigation provided for distal end 22a. In the embodiment described herein, catheter 21 may be used for any suitable therapeutic and/or diagnostic purpose, such as electrical sensing and/or radiofrequency (RF) ablation of tissue in heart 26. To perform its functions, system 20 further includes a temperature sensing module 49, the functions of which are described below.

Physician 30 inserts distal end 22a of shaft 22 through a sheath 23 into a heart 26 of a patient 28 lying on a table 29. Physician 30 navigates the distal end of shaft 22 to a target location in heart 26 by manipulating shaft 22 using a manipulator 32 near the proximal end of the catheter and/or deflection from the sheath 23. During the insertion of distal end 22a, balloon 40 is maintained in a collapsed configuration by sheath 23. By containing balloon 40 in a collapsed configuration, sheath 23 also serves to minimize vascular trauma along the way to target location.

During navigation of distal end 22a in heart 26, console 24 receives signals from magnetic sensor 39 in response to magnetic fields from external field generators 36, for example, for the purpose of measuring the position of ablation balloon 40 in the heart and, optionally, presenting the tracked position on a display 27. Magnetic field generators 36 are placed at known positions external to patient 28, e.g., below patient table 29. Console 24 also comprises a driver circuit 34, configured to drive magnetic field generators 36.

In an embodiment, position signals received from position sensor 39 are indicative of the position of ablation balloon 40 in the coordinate system of position tracking and ablation system 20. The method of position sensing using external magnetic fields is implemented in various medical applications, for example, in the CARTO™ system, produced by Biosense-Webster Inc. (Irvine, California), and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference.

Figure 2:
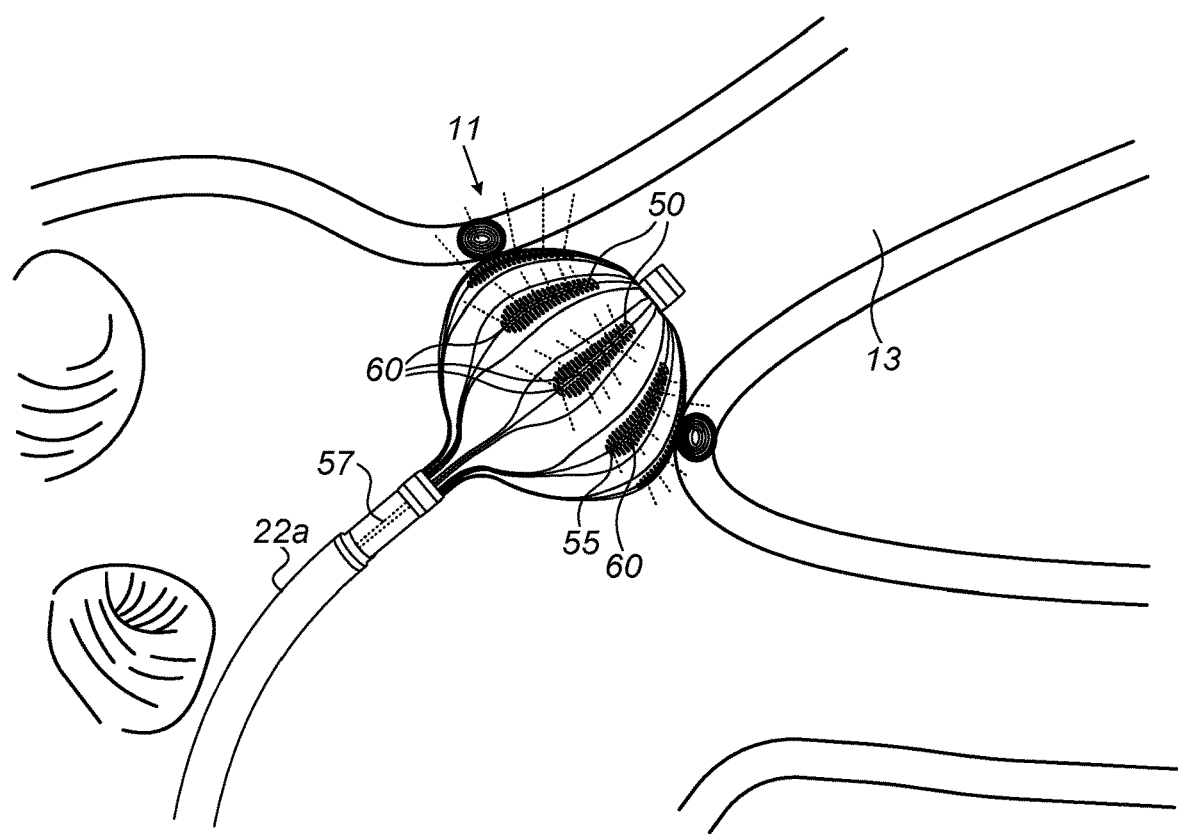
FIG. 2 is a schematic, pictorial side view of a distal end of the balloon catheter of FIG. 1 deployed in the region of a pulmonary vein (PV) and its ostium, in accordance with an embodiment of the invention.

Once distal end 22a of shaft 22 has reached the target location, physician 30 retracts sheath 23 and inflates balloon 40, and further manipulates shaft 22 to bring balloon 40 to contact with an ostium of the pulmonary vein, as described in FIG. 2. As seen, balloon 40 comprises multiple RF ablation electrodes 44 disposed over a perimeter of balloon 40. Each electrode structure includes one or more temperature sensors, shown in FIG. 2.

Control console 24 comprises a processor 41, typically a general-purpose computer, with suitable front end and interface circuits 38 for receiving signals from catheter 21, as well as for applying RF energy treatment via catheter 21 in a left atrium of heart 26 and for controlling the other components of system 20. Processor 41 typically comprises include a software in a memory 48 of system 20, that is programmed to carry out the functions described herein. The software may be downloaded to the computer in electronic form, over a network, for example, or it may, alternatively or additionally, be provided and/or stored on non-transitory tangible media, such as magnetic, optical, or electronic memory. In particular, processor 41 runs a dedicated algorithm as disclosed herein, included in FIG. 4, that enables processor 41 to perform the disclosed steps, as further described below.

Touch Indication of Balloon-Catheter Ablation Electrodes Via Balloon Surface Temperature Measurement FIG. 2 is a schematic, pictorial side view of the balloon catheter of FIG. 1 deployed in the region of a pulmonary vein (PV) 13 and its ostium 11, in accordance with an embodiment of the invention. The balloon catheter is used to ablate ostium 11 to isolate a source of arrhythmia. Balloon 40 may be similar to the balloon used in the HELIOSTAR multi-electrode RF balloon ablation catheter (made by Biosense Webster), which has ten large area electrodes 50 disposed over it. Different levels of RF energy can be delivered independently to each of the ten electrodes, depending on the tissue, during lesion creation. In addition, the HELIOSTAR balloon design makes it possible to achieve isolation, such as PV isolation, with a single application of RF energy.

As seen in FIG. 2, distal end 22a includes an inner lumen 57 through which fluid, such as saline, may flow. Balloon 40 has an exterior membrane formed with irrigation holes 55 through which the fluid (e.g., saline) can exit from the interior of balloon 40 to cool ostium 11 tissue ablation sites. While FIG. 2 shows fluid exiting balloon 40 as jet streams, it is understood that the fluid may exit the balloon with any desired flow rate or pressure, including a rate where the fluid seeps out of the balloon.

As further seen in FIG. 2, the membrane of balloon 40 supports and carries ablation electrodes 50, with one or more temperature sensors 60 included in each electrode structure. Temperatures measured by sensor 60 are used to indicate the touch of ablation electrodes with ostium tissue, as described below.

The pictorial side view shown in FIG. 2 is chosen by way of example, where other embodiments are possible. For example, in another embodiment, cooling fluid can exit through a separate lumen (not shown) and into PV 13, such as a lumen presently used to inject contrast fluid.

Method of Saline Irrigation

Figure 3:
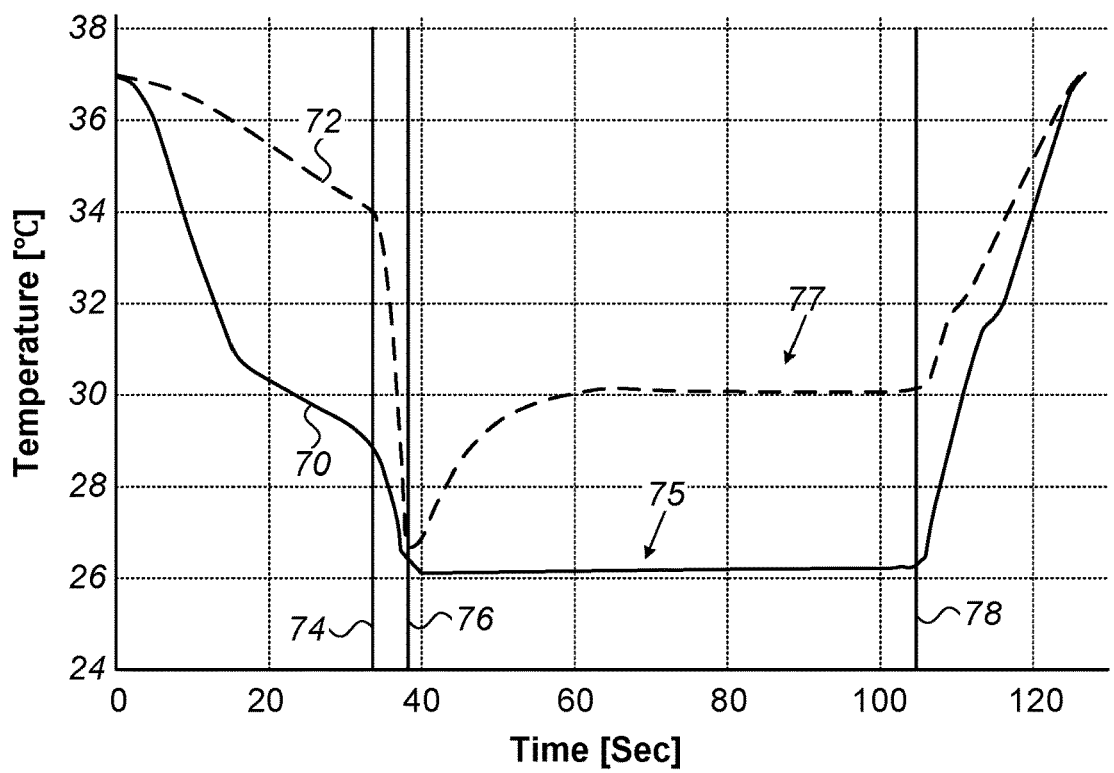
FIG. 3 is a graph showing plots of sensed temperatures in proximity to two ablation electrodes of the balloon catheter of FIG. 1 as a function of time, in accordance with an embodiment of the invention.

FIG. 3 is a graph showing plots 70 and 72 of sensed temperatures in the proximity of two ablation electrodes of the balloon catheter of FIG. 1 as a function of time, in accordance with an embodiment of the invention. Plots 70 and 72 illustrate how temperatures of an electrode 50 that is in contact with tissue, and an electrode 50 that is not in contact, respectively, vary over a period of time during the disclosed touch detection process. Note that the graph does not include an effect of ablation, which is described in FIG. 5.

Initially, at times about t=0 and before, the irrigation is still at a low flow rate (e.g., 5 ml/min), which keeps balloon 40 deflated and the electrode temperatures almost the same as the blood temperature (37° C.). Then, within few seconds after a time t=0, high flow rate (e.g., 35 ml/min) of irrigation is applied, for example, by the physician preparing for ablation. The irrigated saline flows from balloon 40 through irrigation holes 55, as shown in FIG. 2, and also fully inflates balloon 40. At that time, several seconds after time t=0, balloon 40 is already positioned at target tissue, for example, in contact with ostium 11. Balloon 40, being now firmly positioned by the physician in contact with tissue, is presumably occluding PV 13 except, perhaps, for a segmental leakage area.

As is illustrated on the left-hand side (up to t=28 s) there is a significant difference in the resulting temperature vs. time plots of sensors on an occluding electrode (plot 70 shows good contact) and for a non-occluding electrode (plot 72 shows poor contact).

Method of Coolant Injection

At time t=28 S (line 74), the physician injects into PV 13, through a separate lumen, a small one-time amount of a cooled dilution fluid (e.g., 20 ml of saline or glucose at low temperature). This injection, which is performed, manually or automatically by a pump, in a short time interval such as few seconds with exact time depending on volume and injection rate, may also be described as a boost injection (bolus) of cooling fluid.

The injected cooling fluid causes a further rapid drop in blood temperature as sensed by both sensors, but the drop is particularly sharp in plot 72 for poor contact, in which temperature drops from 34° C. to about 27° C. in several seconds after time t=32 S (line 76).

One mechanism that causes the rapid temperature drop is blood flow itself, in which the cooled flowing blood removes heat by convection from the electrode. When the electrode is in contact with tissue, a slower mechanism of heat conduction through tissue, and through the balloon membrane (into a cooler saline inside the balloon), results in a slower and milder effect of temperature reduction.

As seen in FIG. 3, the temperature at the two electrodes have significantly different recovery rates after t=32 S: the occlusion area temperature remains low (~26° C.), while the leakage area temperature quickly increases up to 30° C. As further seen, during times 65<t<105 seconds, periods 75 and 77 of different steady-state temperatures are reached: ~26° C. vs. ~30° C., respectively. The difference of four degrees (4° C.) measured between occluding and non-occluding electrodes can be used to detect partial occlusion as well as where on a perimeter of the balloon partial occlusion occurs, which gives a physician a way to improve balloon catheter contact with ostium 11.

Finally, when releasing the occlusion at a time t=105 S (line 78), the temperature of all electrodes returns to the blood temperature (~37° C.). The occlusion condition is removed, for example, by retracting balloon 40 after an ablation is performed, leaving ostium 11 fully reopened to blood flow.

The plots in FIG. 3 are brought by way of example. Boost injection can be applied standalone or added to irrigation, for example to speed cooling. When irrigation is used alone, similar steady-state temperatures are achieved, of ~26° C. vs. ~0° C. for an electrode that is in contact and an electrode that is not in contact, respectively.

Other fluid types and sensing methods may apply to generate a measurable difference between occluding and non-occluding electrodes. For example, either hypotonic or hypertonic saline may be injected, and a resulting transient blood pressure wave measured by pressure sensors at the electrodes. As noted above, transient chemical properties of blood, such as pH and $CO_2$ content, may also be used with a relevant fluid injected and relevant sensor disposed at the electrodes.

Figure 4:
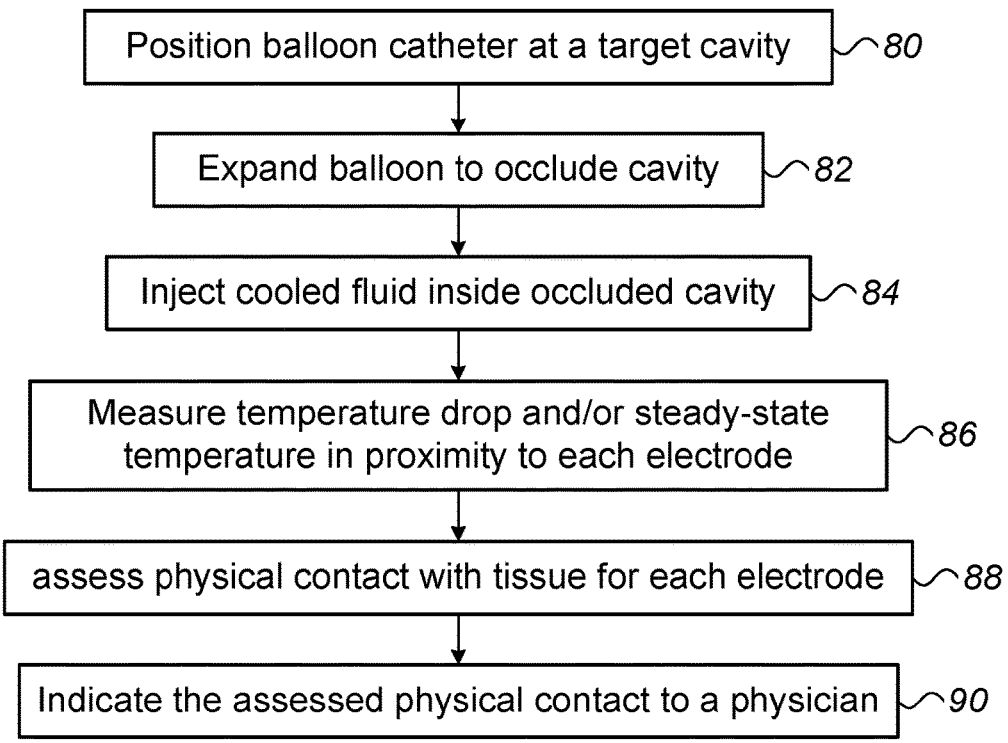
FIG. 4 is a flow chart that schematically illustrates a method of indicating touch of ablation electrodes of the balloon catheter of FIG. 1, in accordance with an embodiment of the invention.

FIG. 4 is a flow chart that schematically illustrates a method of indicating touch of ablation electrodes 50 of the balloon catheter of FIG. 1, in accordance with an embodiment of the invention. The algorithm, according to the presented embodiment, carries out a process that begins when physician 30 positions the balloon catheter at a target location within a cavity of an organ of a patient, such as at ostium 11, at a balloon catheter positioning step 80. Next, physician 30 expands balloon 40, for example by inflating balloon 40 with an increased irrigation rate, to occlude cavity, at a balloon expansion step 82. At this stage, physician 30 may further maneuver balloon 40 to bring expanded balloon 40 into firmer contact with tissue, e.g., over a full circumference of ostium 11. Next, physician 30 injects a cooled fluid through an inner lumen of the catheter, at a coolant injection step 84. At a subsequent temperature monitoring step 86, processor 41 uses measurements from one or more temperature sensors to monitor a resulting temperature in proximity of an ablation electrode. Processor 41 may monitor an amount of temperature drop and/or a steady state temperature reached and maintained for a certain duration (typically few tens of seconds) in the proximity of each electrode.

In a subsequent touch monitoring step 88, processor 41 provides a touch indication per each balloon electrode based on the monitored resulting temperature.

In some embodiments, the touch indication is an audio and/or visual binary indication (touch/no touch). In other embodiments, a fuzzy metric touch indication is used, showing how much the electrode is touching (100%=complete touch, 0%=no touch, 90%=almost complete touch, etc.). The fuzzy indication may be implemented as different color shades, different sound pitches, different sound volumes, a displayed number such as a percentage, a gauge, etc. In some embodiments, processor 41 is further configured to provide a touch index ranging between no-touch and full-touch, and to visually indicate the touch index per balloon electrode.

Finally, at an indicating step 90, processor 41 indicates the assessed physical contact to physician 30.

The example flow chart shown in FIG. 4 is chosen purely for the sake of conceptual clarity. In alternative embodiments, additional steps may be performed, such as an injection of contrast agent followed by fluoroscopy imaging. Contact force sensing may also be applied to monitor the quality of balloon positioning prior to ablation.

Figure 5:
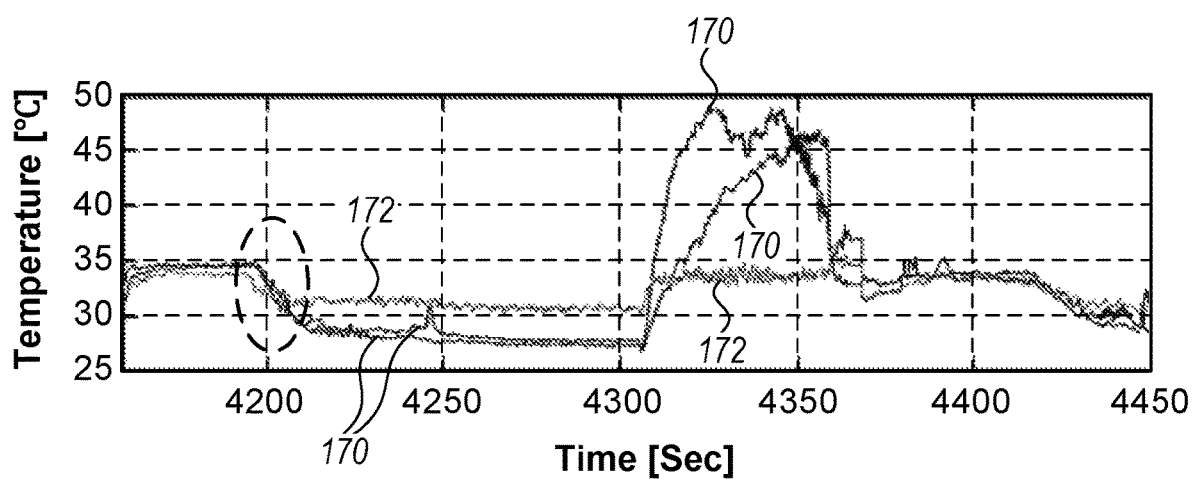
FIG. 5 is a graph that shows sensed temperatures in proximity to ablation electrodes of the balloon catheter of FIG. 1 as a function of time, including during an RF ablation, in accordance with an embodiment of the invention.

FIG. 5 is a graph that shows sensed temperatures in proximity to ablation electrodes of the balloon catheter of FIG. 1 as a function of time, including during an RF ablation, in accordance with an embodiment of the invention. FIG. 5 was obtained during a clinical study of the disclosed technique.

As seen, plots 170 and 172 illustrate how temperatures of two electrodes 50 that are in good contact with tissue, and of an electrode 50 that is not in contact, respectively, vary over a period of time during the disclosed touch detection process.

Initially, at times before t=4200 Sec, the irrigation is still at a low flow rate (e.g., 5 ml/min), which keeps balloon 40 deflated and the electrode temperatures slightly below blood temperature (i.e., at about 35° C.). Then, within few seconds after a time t=4200 Sec, high flow rate (e.g., 35 ml/min) of irrigation is applied by the physician preparing for ablation.

As is illustrated in FIG. 5, just after t=4200 Sec a significant difference develops between the resulting temperature vs. time plots of sensors on occluding electrodes (plot 170 shows good contact) and for a sensor of a non-occluding electrode (plot 172 shows poor contact).

At a steady-state temperature phase, during times 4260<t<4310, the temperature in the two occlusion areas remains low (~27.5° C.), while the leakage area temperature quickly increases up to 31° C. Typically, the temperature of an electrode in poor contact with tissue will be more affected by blood temperature (i.e., ~37° C.), which causes the quick increase in temperature in the leakage area, as seen plot 172.

As further seen, during RF ablation, at times 4310<t<4360 seconds, the electrodes found by the disclosed technique to be in good contact with tissue reaches a clinically effective ablative temperature in the range of 45° C.-50° C. The electrode found by the disclosed technique to be in bad contact with tissue cannot largely be heated above 35° C., on the other hand, as it dissipates the RF energy into the surrounding flowing blood.

In addition to measuring temperature, it may be possible to measure impedance between each of the ablation electrodes and a surface electrode attached to the skin of the patient. Variations in the impedance may be observable at a timing when electrode contacts tissue, in correspondence with the significant drop of temperature of the occluding electrodes (i.e., in good correspondence with plot 170). On the other hand, the impedance response is expected to remain flat (as a function of time) for the non-occluding electrode, as the electrode is still immersed in blood after the balloon was inflated. Using both detection methods (i.e., temperature change and impedance response) may improve the accuracy of the disclosed technique.

Although the embodiments described herein mainly address pulmonary vein isolation, the methods and systems described herein can also be used in other applications that require a determination of occlusion, such as in electrophysiological mapping and renal denervation.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method, comprising:
   positioning an expandable balloon, coupled to a distal end of a catheter, at a target location within an organ of a patient, the expandable balloon comprising multiple electrodes and one or more sensors in proximity to each electrode, wherein the one or more sensors are configured each to measure a pH of blood, a temperature of blood, or a carbon dioxide content of blood in proximity to each electrode;
   expanding the expandable balloon at the target location;
   flowing a fluid through an inner lumen of the catheter and into the blood in a vicinity of each electrode to cause the pH, the temperature, or the carbon dioxide content of blood to be transient;
   measuring, at the target location, over a period of time and in an ongoing state, and via the one or more sensors, a dependence of the pH, the temperature, or the carbon dioxide content of blood on time over the period of time and in the ongoing state in proximity to each electrode;
   determining, in the ongoing state, using a processor, whether or not each electrode is in physical contact with tissue at the target location over the period of time, based on the measured dependence of the pH, the temperature, or the carbon dioxide content of blood on time over the period of time; and
   outputting to a user an indication of whether or not each electrode is in physical contact with the tissue at the target location over the period of time.

2. The method according to claim 1, wherein flowing the fluid comprises continuously applying irrigation fluid via the balloon.

3. The method according to claim 1, wherein flowing the fluid comprises bolus-injecting the fluid.

4. The method according to claim 1, wherein each of the one or more sensors comprises a temperature sensor.

5. The method according to claim 1, wherein each of the one or more sensors comprises a pH sensor.

6. The method according to claim 1, wherein determining whether or not each electrode is in physical contact with tissue comprises determining a baseline of the of blood, and comparing the baseline to the measured dependence on time of the pH, temperature, or the carbon dioxide content over the period of time.

7. The method according to claim 6, wherein determining the baseline comprises measuring the pH, the temperature, or the carbon dioxide content of blood using the one or more sensors of an electrode deliberately maneuvered not to be in contact with the tissue over the period of time.

8. The method according to claim 1, wherein determining whether or not each electrode is in physical contact with tissue comprises estimating, over the period of time and while the balloon is at the target location, a rate with which the pH, the temperature, or the carbon dioxide content of blood returns to an original value after stopping flow of the fluid.

9. The method according to claim 1, wherein determining whether or not each electrode is in physical contact with tissue comprises estimating, over the period of time and while the balloon is at the target location, a time duration from a beginning of flow of the fluid until the pH, the temperature, or the carbon dioxide content of blood reaches a steady-state value.

10. The method according to claim 1, wherein determining whether or not each electrode is in physical contact with tissue comprises determining, over the period of time, an extremum value of the pH, the temperature, or the carbon dioxide content of blood reached in vicinity of each electrode.

11. The method according to claim 1, wherein measuring, at the target location and over the period of time, the dependence of the pH, the temperature, or the carbon dioxide content of blood comprises comparing the pH, the temperature, or the carbon dioxide content with a calibrated pH, a calibrated temperature, or a calibrated carbon dioxide content.

12. The method according to claim 1, wherein the fluid comprises a coolant.

13. The method according to claim 1, wherein the fluid comprises saline.

14. The method according to claim 1, wherein flowing the fluid comprises injecting the fluid through a lumen used for injecting contrast fluid.

15. The method according to claim 1, wherein flowing the fluid comprises injecting the fluid through irrigation holes in the balloon.

16. The method according to claim 1, wherein a cavity of the organ comprises one of a pulmonary vein of the heart and a left atrium of the heart.

17. The method of claim 1, wherein determining whether or not each electrode is in physical contact with tissue comprises determining an amount of each electrode that is in physical contact with the tissue, the amount ranging from no physical contact to full physical contact with the tissue, and wherein outputting to a user an indication of whether or not each electrode is in physical contact with the tissue comprises outputting to a user an indication of the amount each electrode is in physical contact with the tissue.

18. The method of claim 1, wherein the measured dependence of the pH, the temperature, or the carbon dioxide content of blood on time over the period of time and in the ongoing state comprises a temperature profile.

19. A system, comprising:
a catheter, comprising:
  a shaft for insertion into a cavity of an organ of a patient at a target location within the organ, the shaft having an inner lumen for flowing a fluid to cause a pH of blood, a temperature of blood, or a carbon dioxide content of blood to be transient; and
  an expandable balloon, coupled to a distal end of the shaft, the expandable balloon comprising multiple electrodes and one or more sensors in proximity to each electrode, the one or more sensors being configured each to measure the pH, the temperature, or the carbon dioxide content of blood in proximity to each electrode at the target location over a period of time and in an ongoing state; and
a processor, which is configured to,
  determine, in the ongoing state, whether or not each electrode is in physical contact with tissue at the target location over the period of time, based on a measured dependence of the pH, the temperature, or the carbon dioxide content of blood on time over the period of time; and
  output to a user an indication of whether or not each electrode is in physical contact with the tissue at the target location over the period of time.

20. The system according to claim 19, wherein each of the one or more sensors comprises a temperature sensor.

21. The system according to claim 19, wherein each of the one or more sensors comprises a pH sensor.

22. The system according to claim 19, wherein the processor is configured to determine whether or not each electrode is in physical contact with tissue by determining a baseline of the pH, the temperature, or the carbon dioxide content of blood, and comparing the baseline to the measured dependence on time of the pH, temperature, or the carbon dioxide content over the period of time.

23. The system according to claim 19, wherein the processor is configured to determine whether or not each electrode is in physical contact with tissue by estimating a rate, over the period of time and while the balloon is at the target location, with which the the pH, the temperature, or the carbon dioxide content of blood returns to an original value after stopping flow of the fluid.

24. The system according to claim 19, wherein the processor is configured to determine whether or not each electrode is in physical contact with tissue by estimating, over the period of time and while the balloon is at the target location, a time duration from a beginning of flow of the fluid until the characteristic of blood reaches a steady-state value.

25. The system according to claim 19, wherein the processor is configured to determine whether or not each electrode is in physical contact with tissue by determining, over the period of time, an extremum value of the pH, the temperature, or the carbon dioxide content of blood reached in vicinity of each electrode.

26. The system according to claim 19, wherein the processor is configured to measure, at the target location and over the period of time, a dependence of the pH, the temperature, or the carbon dioxide content of blood on time by comparing the pH, the temperature, or the carbon dioxide content with a calibrated pH, a calibrated temperature, or a calibrated carbon dioxide content.

27. The system according to claim 19, wherein the fluid comprises a coolant.

28. The system according to claim 19, wherein the fluid comprises saline.

29. The system according to claim 19, wherein the cavity comprises one of a pulmonary vein of the heart and a left atrium of the heart.

30. The system of claim 19, wherein the processor is further configured to:
  determine an amount of each electrode that is in physical contact with the tissue, the amount ranging from no physical contact to full physical contact with the tissue; and
  output to a user an indication of the amount each electrode is in physical contact with the tissue.

31. The system of claim 19, wherein the measured dependence of the pH, the temperature, or the carbon dioxide content of blood on time over the period of time and in the ongoing state comprises a temperature profile.

32. A system, comprising:
  a catheter, comprising:
    a shaft for insertion into a cavity of an organ of a patient at a target location within the organ, the shaft having an inner lumen for flowing a fluid to cause a pH of blood, temperature, and carbon dioxide content to be transient; and
    an expandable balloon, coupled to a distal end of the shaft, the expandable balloon comprising multiple electrodes and one or more sensors in proximity to each electrode, the one or more sensors being configured each to measure the pH, the temperature, or the carbon dioxide content of the blood in dependence on time at the target location over a period of time and in an ongoing state; and
  a processor, which is configured to,
    determine, in the ongoing state, an amount of each electrode that is in physical contact with tissue at the target location over the period of time, the amount ranging from no physical contact to full physical contact with the tissue, based on the measured dependence on time of the pH, the temperature, or the carbon dioxide content of the blood over the period of time; and
    output to a user an indication of the amount each electrode is in physical contact with the tissue at the target location over the period of time.

33. The system of claim 32, wherein the measured dependence on time of the pH, the temperature, or the carbon dioxide content of blood over the period of time and in the ongoing state comprises a temperature profile.

* * * * *